(12) United States Patent
Narayan et al.

(10) Patent No.: US 9,037,251 B2
(45) Date of Patent: May 19, 2015

(54) ARTIFICIAL RETINA DEVICE

(75) Inventors: Kavassery Sureswaran Narayan, Bangalore (IN); Vini Gautam, New Delhi (IN); Monojit Bag, Bangalore (IN)

(73) Assignee: JAWAHARLAL NEHRU CENTRE FOR ADVANCED SCIENTIFIC RESEARCH, Bangalore, Karnataka (IN)

( * ) Notice: Subject to any disclaimer, the term of this patent is extended or adjusted under 35 U.S.C. 154(b) by 188 days.

(21) Appl. No.: 13/124,357

(22) PCT Filed: Sep. 2, 2010

(86) PCT No.: PCT/IB2010/002170
§ 371 (c)(1),
(2), (4) Date: Apr. 14, 2011

(87) PCT Pub. No.: WO2012/001454
PCT Pub. Date: Jan. 5, 2012

(65) Prior Publication Data
US 2012/0065704 A1    Mar. 15, 2012

(30) Foreign Application Priority Data

Jun. 28, 2010   (IN) ............ 1822/CHE/2010

(51) Int. Cl.
*A61N 1/05*       (2006.01)
*A61N 1/36*       (2006.01)
*B82Y 10/00*      (2011.01)
*H01L 51/00*      (2006.01)
*H01L 51/42*      (2006.01)

(52) U.S. Cl.
CPC ........... *A61N 1/36046* (2013.01); *A61N 1/0543* (2013.01); *B82Y 10/00* (2013.01); *H01L 51/0036* (2013.01); *H01L 51/0047* (2013.01); *H01L 51/4253* (2013.01)

(58) Field of Classification Search
USPC .......................................... 607/116; 623/6.63
See application file for complete search history.

(56) References Cited

U.S. PATENT DOCUMENTS 4,870,268 A    9/1989    Vincent et al.
5,424,974 A *  6/1995    Liu et al. .................... 365/112
(Continued)

FOREIGN PATENT DOCUMENTS

CN    101149559 A    3/2008
EP    1 207 556      5/2002
(Continued)

OTHER PUBLICATIONS

Asplund, M. L. M., et al., "Neural Microcontacts with Wire Electrodes and Woven Logic," Materials Research Society Spring Meeting, 2007, downloaded from http://www.mrs.org/smrs/doc.asp?CID=8697&DID=193935, 1 p.
(Continued)

*Primary Examiner* — Carl H Layno
*Assistant Examiner* — Jon Eric C Morales
(74) *Attorney, Agent, or Firm* — Foley & Lardner LLP

(57) ABSTRACT

The present technology provides an organic based artificial retina device that includes a substrate and an array of micro-electrodes formed on the substrate. The illustrative artificial retina device further includes a photoconducting polymer blend deposited on the array of micro-electrodes. The photoconducting polymer blend is configured to produce a photoelectric signal in response to receiving light.

22 Claims, 13 Drawing Sheets

(56) References Cited

U.S. PATENT DOCUMENTS

| | | | |
|---|---|---|---|
| 5,965,875 | A | 10/1999 | Merrill |
| 6,324,429 | B1 | 11/2001 | Shire et al. |
| 6,611,716 | B2 | 8/2003 | Chow et al. |
| 7,003,354 | B2 | 2/2006 | Chow et al. |
| 7,031,776 | B2 | 4/2006 | Chow et al. |
| 7,079,900 | B2 | 7/2006 | Greenburg et al. |
| 7,139,612 | B2 | 11/2006 | Chow et al. |
| 7,272,447 | B2 | 9/2007 | Stett et al. |
| 7,774,931 | B2 * | 8/2010 | Tai et al. ............ 29/832 |
| 2003/0097165 | A1 | 5/2003 | Krulevitch et al. |
| 2003/0097166 | A1 * | 5/2003 | Krulevitch et al. ....... 607/116 |
| 2004/0267344 | A1 | 12/2004 | Stett et al. |
| 2007/0095669 | A1 * | 5/2007 | Lau et al. .......... 204/547 |
| 2007/0142878 | A1 | 6/2007 | Krulevitch et al. |
| 2008/0288067 | A1 * | 11/2008 | Flood ............ 623/6.63 |
| 2009/0210055 | A1 | 8/2009 | Chang et al. |
| 2009/0292325 | A1 | 11/2009 | Cederna et al. |
| 2010/0155707 | A1 | 6/2010 | Anthopoulos |

FOREIGN PATENT DOCUMENTS

| | | |
|---|---|---|
| WO | WO-2008/122778 | 10/2008 |
| WO | WO-2008/141271 | 11/2008 |
| WO | WO-2009/143625 | 12/2009 |

OTHER PUBLICATIONS

Basinger, B. C., et al., "Finite element modeling of retinal prosthesis mechanics," *Journal of Neural Engineering*, 2009, vol. 6, No. 5, 9 pp.

Güven, D., et al., "Long-term stimulation by active epiretinal implants in normal and RCD1 dogs*," *Journal of Neural Engineering*, 2005, vol. 2, No. 1, pp. S65-S73.

Ahuja, A.K. et al., "An In Vitro Model of a Retinal Prosthesis," IEEE Transactions on Biomedical Engineering, Jun. 2008, vol. 55, No. 6, pp. 1744-1753.

Ahuja, A.K. et al., "The Dependence of Spectral Impedance on Disc Microelectrode Radius," IEEE Transactions on Biomedical Engineering, Apr. 2008, vol. 55, No. 4, pp. 1457-1460.

Antognazza, M. R. et al., "Organic-based tristimuli colorimeter," Appl. Phys. lett., 2007, vol. 90, pp. 163509-1-163509-3.

Behrend, M.R. et al., "Selective Labeling of Retinal Ganglion Cells with Calcium Indicators by Retrograde Loading In Vitro," Journal of Neuroscience Methods, 2009, vol. 179, pp. 166-172.

Behrend, M.R. et al., "Dynamic Current Density of the Disk Electrode Double-Layer," IEEE Transactions on Biomedical Engineering, Mar. 2008, vol. 55, No. 3, pp. 1056-1062.

Caspi, A. et al., "Feasibility Study of a Retinal Prosthesis: Spatial Vision with a 16-Electrode Implant," Arch Ophthalmol, Apr. 2009, vol. 127, No. 4, pp. 398-401.

Colodetti, L. et al., "Pathology of Damaging Electrical Stimulation in the Retina," Experimental Eye Research, 2007, 85, pp. 23-33.

De Balthasar, C. et al., "Factors Affecting Perceptual Thresholds in Epiretinal Prostheses," Investigative Ophthalmology and Visual Science, Jun. 2008, vol. 49, No. 6, pp. 2303-2314.

Green, R. A. et al., "Conducting polymers for neural interfaces: Challenges in developing an effective long-term implant," Biomaterials, 2008, vol. 29, pp. 3393-3399.

Greenbaum, E. et al., "Metabolic Prosthesis for Oxygenation of Ischemic Tissue," IEEE Transactions on Biomedical Engineering, Feb. 2009, vol. 56, No. 2, pp. 528-531.

Greenwald, S.H. et al., "Brightness as a Function of Current Amplitude in Human Retinal Electrical Stimulation," Investigative Ophthalmology & Visual science, Nov. 2009, vol. 50, No. 11, pp. 5017-5025.

Gurunathan, K. et al., "Review: Electrochemically synthesized conducting polymeric materials for applications towards technology in electronics, optoelectronics and energy storage devices," Materials Chemistry and Physics, 1999, vol. 61, pp. 173-191.

Güven, D. et al., "Implantation of an Inactive Epiretinal Poly (Dimethyl Siloxane) Electrode Array in Dogs," Experimental Eye Research, 2006, vol. 82, pp. 81-90.

Horsager, A. et al., "Predicting Visual Sensitivity in Retinal Prosthesis Patients," Investigative Ophthalmology and Visual Science, Apr. 2009, vol. 50, No. 4, pp. 1483-1491.

Kendir, G.A. et al., "An Optimal Design Methodology for Inductive Power Link with Class-E Amplifier," IEEE Transactions on Circuits and Systems—I: Regular Papers, May 2005, vol. 52, No. 5, pp. 857-866.

Kim, J. et al., "A Fully Integrated DPSK Demodulator for High Density Biomedical Implants," Proceedings of Biomedical Circuits and Systems Conference, 2008, pp. 93-96.

Lazzi, G., "Thermal Effects of Bioimplants: Power Dissipation Characteristics and Computational Methods," IEEE Engineering in Medicine and Biology Magazine, Sep./Oct. 2005, pp. 75-81.

Mahadevappa, M. et al., "Perceptual Thresholds and Electrode Impedance in Three Retinal Prosthesis Subjects," IEEE Transactions on Neural Systems and Rehabilitation Engineering, Jun. 2005, vol. 13, No. 2, pp. 201-206.

Meixner, R. M. et al., "Wavelength-selective organic field-effect phototransistors based on dye-doped poly-3-hexylthiophene," Appl. Phys. Lett., 2006, vol. 89, pp. 092110-1-092110-3.

Pennisi, C. P. et al., "Spatial Distribution of the Electric Potential from Photosystem I Reaction Centers in Lipid Vesicles," IEEE Transactions on Nanobioscience, Jun. 2008, vol. 7, No. 2, pp. 164-171.

Pennisi, C.P. et al., "Incorporation of Photosynthetic Reaction Centers in the Membrane of Human Cells: Toward a New Tool for Optical Control of Cell Activity," Cellular and Molecular Bioengineering, Mar. 2009, vol. 2, No. 1, pp. 156-165.

Ray, A. et al., "Immunocytochemical Analysis of Retinal Neurons under Electrical Stimulation," Brain Res. Author manuscript, Published in final edited form as: Brain Res., Feb. 19, 2009, vol. 1255, pp. 89-97 (14 pages).

Rodger, D.C. et al., "Flexible Parylene-Based Multielectrode Array Technology for High-Density Neural Stimulation and Recording," Sensors and Actuators B, 2008, vol. 132, pp. 449-460.

Roizenblatt, R. et al., "Nanobiolistic Delivery of Indicators to the Living Mouse Retina," Journal of Neuroscience Methods, 2006, vol. 153, pp. 154-161.

Sanders, C. et al., "Dynamic Interactions of Retinal Prosthesis Electrodes with Neural Tissue and Materials Science in Electrode Design," Artificial Sight, 2008, pp. 209-226.

Shah, S. et al., "Electrical Properties of Retinal-Electrode Interface," Journal of Neural Engineering, 2007, vol. 4, pp. S24-S29.

Singh, V. et al., "On the Thermal Elevation of a 60-Electrode Epiretinal Prosthesis for the Blind," IEEE Transactions on Biomedical Circuits and Systems, Dec. 2008, vol. 2, No. 4, pp. 289-300.

Singh, V. et al., "Specific Absorption Rate and Current Densities in the Human Eye and Head Induced by the Telemetry Link of a Dual-Unit Epiretinal Prosthesis," IEE Transactions on Antennas and Propagation, Oct. 2009, vol. 57, No. 10, pp. 3110-3118.

Sivaprakasam, M. et al., "Architecture Tradeoffs in High-Density Microstimulators for Retinal Prosthesis," IEEE Transactions on Circuits and Systems, Part 1, Regular Papers, Dec. 2005, vol. 52, No. 12, pp. 2629-2641.

Weiland, J.D et al., "Visual Prosthesis," Proceedings of the IEEE, Jul. 2008, vol. 96, No. 7, 9 pages.

Weiland, J.D. et al., "A Biomimetic Retinal Stimulating Array: Design Considerations," IEEE Engineering in Medicine and Biology Magazine, Sep./Oct. 2005, pp. 14-21.

Weiland, J.D. et al., "Retinal Prosthesis," Annu. Rev. Biomed. Eng., 2005, vol. 7, pp. 361-401, C-1-C-4.

Wu, L. et al., "An Efficient Wireless Power Link for High Voltage Retinal Implant," Proceedings of Biomedical Circuits and Systems Conference (BioCAS), Baltimore, MD, Nov. 20-22, 2008, 4 pages.

Xiao, X. et al., "In Vitro and in Vivo Evaluation of Ultrananocrystalline Diamond for Coating of Implantable Retinal Microchips," Journal of Biomedical Materials Research Part B: Applied Biomaterials, 2006, vol. 77, pp. 273-281.

Yanai, D. et al., Visual Performance Using a Retinal Prosthesis in Three Subjects with Retinitis Pigmentosa, American Journal of Ophthalmology, May 2007, vol. 143, No. 5, pp. 820-827.e2.

(56) References Cited

OTHER PUBLICATIONS

Zhou, M. et al., "A Non-Coherent DPSK Data Receiver with Interference Cancellation for Dual-Band Transcutaneous Telemetries," IEEE Journal of Solid-State Circuits, Sep. 2008, vol. 43, No. 9, pp. 2003-2012.

Ghezzi, D., et al., "A hybrid bioorganic interface for neuronal photoactivation," *Nature Communications*, 2011, vol. 2, No. 166, pp. 1-7, Macmillan Publishers Limited.

Bharath A., et al., "Next Generation Artificial Vision Systems Reverse Engineering the Human Visual System," 2008, Artech House, Inc., Ch. 10.4.2 to 10.5, Fig 10.8, pp. 264 and 271-288.

International Search Report and Written Opinion received for PCT/IB2012/053711 dated Oct. 2, 2012.

Lawrence Livermore National Laboratory, "Using Micro-Fabrication Methods to Further Develop Biocompatible Microelectrode Array for Artificial Retina Device," Feb. 4, 2012, 3 pages, retrieved from: http://www.azonano.com/news.aspx?newsID=15783 on Feb. 5, 2013.

Rao, M. et al., "Studies of Photogenerated Charge Carriers from Donor-Acceptor Interfaces in Organic Field Effect Transistors. Implications for Organic Solar Cells," 2010, J. Phys. Chem. C, vol. 114, No. 48, pp. 20609-20613.

Antognazza, M. R. et al., "A hybrid solid-liquid polymer photodiode for the bioenvironment," Appl. Phys. Lett., vol. 94, 2009, pp. 243501-1-243501-3.

Arun, N. et al., "Conducting Polymers as Antennas for Probing Biophysical Activities," J. Phys. Chem. B, vol. 112, 2008, pp. 1564-1569.

Blau, A. et al., "Prototyping all-polymer bioelectrical signal transducers," IFMBE Proceedings, vol. 25, 2009, pp. 327-330.

Chow, A. Y. et al., "Implantation of Silicon Chip Microphotodiode Arrays into the Cat Subretinal Space," IEEE Transactions on Neural Systems and Rehabilitation Engineering, vol. 9, No. 1, Mar. 2001, pp. 86-95.

De Paoli, Marco-A. et al., "Electrochemistry, Polymers and Opto-Electronic Devices: A Combination with a Future," J. Braz. Chem. Soc., 2002, vol. 13, No. 4, pp. 410-424.

Gao, J. et al., "Polymer p-i-n Junction Photovoltaic Cells," Adv. Mater., 1998, vol. 10, No. 9, pp. 692-695.

Gupta, D. et al., "Transport of Photogenerated Charge Carriers in Polymer Semiconductors," Proceedings of the IEEE, Sep. 2009, vol. 97, No. 9, pp. 1558-1569.

International Search Report and Written Opinion for PCT/IB2010/002170 mailed Jan. 14, 2011.

Kabra, D. et al., "Charge carrier dynamics in organic semiconductors by position dependent optical probing," J. Appl. Phys., 2007, vol. 101, pp. 064510-1-064510-7.

Kabra, D. et al., "Model for Studies of Lateral Photovoltaic Effect in Polymeric Semiconductors," IEEE Sensors Journal, Oct. 2008, vol. 8, No. 10, pp. 1663-1671.

Nyberg, T. et al., "Ion conducting polymer microelectrodes for interfacing with neural networks," Journal of Neuroscience Methods, 2007, vol. 160, pp. 16-25.

Optobionics webpage, "ASR Device," printed on Jun. 23, 2010, retrieved from the internet:<URL: http://www.optobionics.com/asrdevice.shtml>, 1 page.

RLE Progress Report, "Chapter 17. The Retinal Implant Project," retrieved from the internet:<URL: http://www.rle.mit.edu/rleonline/ProgressReports/2104_17.pdf>, 12 pages, May 2007.

Second Sight Medical Products, Inc. webpage, "About Us," printed on Jun. 23, 2010, retrieved from the internet:<URL: http://www.2-sight.com>, 1 page.

Seo, Jong-Mo. et al., "Biocompatibility of polyimide microelectrode array for retinal stimulation," Materials Science and Engineering C, 2004, vol. 24, pp. 185-189.

Simon, J., "Molecular Solar Cells. Part 1: Devices based on Easily Doped Insulators," International Journal of Applied Chemistry, 2007, vol. 3, No. 3, pp. 167-211.

Yagi Laboratory—Tokyo Institute of Technology webpage, "Visual Prosthesis (Retinal Implant & Biohybrid Retinal Implant)," printed on Jun. 23, 2010, retrieved from the internet:<URL: http://www.io.mei.titech.ac.jp/research/retina/index.html>, 5 pages.

Azonano webpage, "Using Micro-Fabrication Methods to Further Develop Biocompatible Microelectrode Array for Artificial Retina Device," Posted Feb. 4, 2010, retrieved from the internet:<URL: http://www.azonano.com/news.asp?NewsID=15783>, 2 pages.

Yu, G. et al., "Large-Area, Full-Color Image Sensors Made with Semiconducting Polymers," Adv. Mater., 1998, vol. 10, No. 17, pp. 1431-1434.

An, K. H. et al., "Organic photodetector with spectral response tunable across the visible spectrum by means of internal optical microcavity," Organic Electronics, vol. 10, pp. 1152-1157, (2009).

Bag, M. and Narayan, K. S., "Universality in the intensity-modulated photocurrent in bulk-heterojunction polymer solar cells," Phys. Rev. B., vol. 82, 075308, pp. 1-13, (2010).

Boyer, A. et al., "Colour Discrimination by Forward And Reverse Photocurrents in Bacteriorhodopsin-Based Photosensor," Biosensors and Bioelectronics, vol. 10, No. 5, pp. 415-422, (1995).

Boynton, R. M., "Rapid Chromatic Adaptation and the Sensitivity Functions of Human Color Vision," J. Opt. Soc. Am. 46, 172-179, (1956).

Butterwick, A. et al., "Effect of shape and coating of a subretinal prosthesis on its integration with the retina," Experimental Eye Research, vol. 88, pp. 22-29, (2009).

Chen, E-C. et al., "Polymer photodetector with voltage-adjustable photocurrent spectrum," Applied Physics Letters, vol. 96, pp. 043507-043507-3, (Jan. 29, 2010).

Chow, A. Y. et al. "The artificial silicon retina microchip for the treatment of vision loss from retinitis pigmentosa," Arch. Ophthalmol., vol. 122, No. 4, pp. 460-469 (Apr. 2004).

Clark, J. and Lanzani, G., "Organic photonics for communications," Nat Photon, vol. 4, pp. 438-446, (Jul. 2010).

Dacey, D. M., "Parallel pathways for spectral coding in primate retina," Annu. Rev. Neurosci., vol. 23, pp. 743-775, (2000).

Durban, M. M. et al., "Synthesis and Characterization of Thiophene-Containing Naphthalene Diimide n-Type Copolymers for OFET Applications," Macromolecules, vol. 43, No. 15, pp. 6348-6352, (2010).

Field, G. D. and Chichilnisky, E. J., "Information processing in the primate retina: Circuitry and coding," Annual Review of Neuroscience, vol. 30, p. 1-30, (Jul. 2007).

Forrest, S. R., "The path to ubiquitous and low-cost organic electronic appliances on plastic," Nature 428, pp. 911-918, (Apr. 29, 2004).

Gautam, V. et al., "Dynamics of Bulk Polymer Heterostructure/Electrolyte Devices," J. Phys. Chem. Lett. vol. 1, No. 22, pp. 3277-3282, (2010).

Gong, X. et al., "High-Detectivity Polymer Photodetectors with Spectral Response from 300 nm to1450 nm," Science, vol. 325, No. 5948, pp. 1665-1667, (Aug. 13, 2009).

Graber, P. and Trissl, H.-W., "On the rise time and polarity of the photovoltage generated by light gradients in chloroplast suspensions," FEBS Letters, vol. 123, No. 1, pp. 95-99, (Jan. 1981).

Halls, J. J. M. et al., "Efficient photodiodes from interpenetrating polymer networks," Nature 376,498-500 (1995).

Humayun, M. S. et al., "Pattern electrical stimulation of the human retina," Vision Research, vol. 39, pp. 2569-2576, (1999).

Humayun, M. S. et al., "Visual perception in a blind subject with a chronic microelectronic retinal prosthesis," Vision Research, vol. 43, No. 24, pp. 2573-2581, (Nov., 2003).

Lörinczi, É. et al., "Voltage- and pH-Dependent Changes in Vectoriality of Photocurrents Mediated by Wild-type and Mutant Proteorhodopsins upon Expression in Xenopus Oocytes," J. of Mol. Bio., vol. 393, No. 2, pp. 320-341, (Oct. 23, 2009).

Macadam, D. L., "Chromatic Adaptation," J. Opt. Soc. Am, vol. 46, No. 7, pp. 500-513, (1956).

MRS Website: HH: Organic Photovoltaic Science and Technology, accessed at http://www.mrs.org/s_mrs/doc.asp?CID=25913&DID=307625, published on Apr. 5-9, 2010, p. 86.

Nassi, J. J. and Callaway, E. M., "Parallel processing strategies of the primate visual system," Nature Reviews Neuroscience, vol. 10, pp. 360-372, (May 2009).

(56) References Cited

OTHER PUBLICATIONS

Paillotin, G. et al., "Why does the light-gradient photovoltage from photosynthetic organelles show a wavelength-dependent polarity?," Biophys. J, vol. 65, No. 1, pp. 379-385, (Jul. 1993).

Punke, M. et al., "Dynamic characterization of organic bulk heterojunction photodetectors," Applied Physics Letters, vol. 91, Issue 7, pp. 071118-071118-3, (Aug. 2007).

Rizzo, J. F. et al., "Methods and perceptual thresholds for short-term electrical stimulation of human retina with microelectrode arrays," Invest. Ophthalmol. and Vis. Sci., vol. 44, No. 12, pp. 5355-5361, (Dec. 2003).

Schilinsky, P. et al., "Polymer photovoltaic detectors: progress and recent developments," Thin Solid Films, vols. 451-452, pp. 105-108, (Mar. 2004).

Schilinsky, P. et al., "Recombination and loss analysis in polythiophenebased bulk heterojunction photodetectors," Applied Physics Letters, vol. 81, Issue 20, pp. 3885-3887, (Nov. 2002).

Shoval, A. et al., "Carbon nanotube electrodes for effective interfacing with retinal tissue," Frontiers in Neuroengineering, vol. 2, No. 4, pp. 1-8, (2009).

Solomon, S. G. et al., "The machinery of colour vision," Nat. Rev. Neurosci., vol. 8, No. 4, pp. 276- 286, (Apr. 2007).

Szendrei, K. et al., "Ambipolar all-polymer bulk heterojunction field-effect transistors," Journal of Materials Chemistry, vol. 20, pp. 1317-1321, (2010).

Wang, X. et al., "Integrated thin-film polymer/fullerene photodetectors for on-chip microfluidic chemiluminescence detection," Lab on a Chip, vol. 7, pp. 58-63, (2007).

Xu, T. et al., "Plasmonicnanoresona-tors for high-resolution colourfiltering and spectral imaging," Nat. Commun., vol. 1, Article 59, pp. 1-15, (2010).

Yan, H. et al. "A high-mobility electron-transporting polymer for printed transistors," Nature, vol. 457, pp. 679-686, (Feb. 5, 2009).

Kim et al., "A strong regioregularity effect in self-organizing conjugated polymer films and high-efficiency polythiophene:fullerene solar cells," Nature Materials, vol. 5, Mar. 2006, pp. 197-203.

Non-Final Office Action in U.S. Appl. No. 14/235,603 dtd Jan. 26, 2015 (11 pages).

* cited by examiner

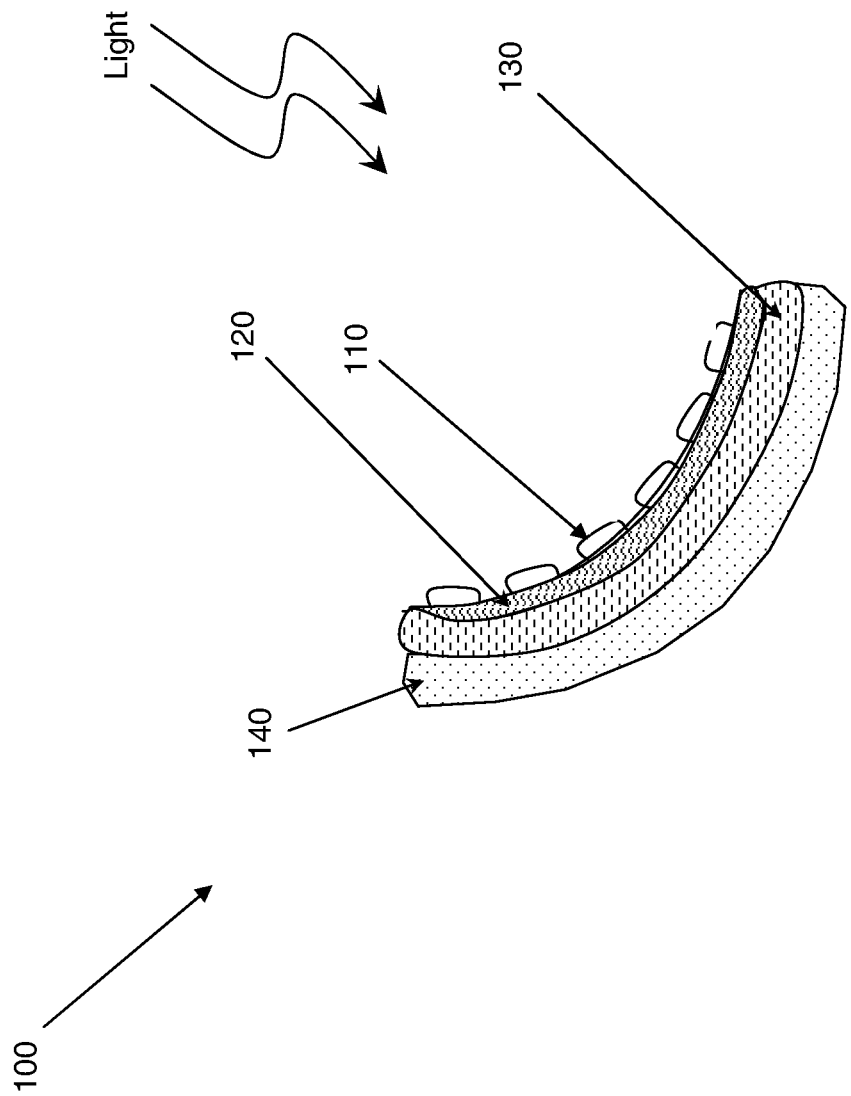

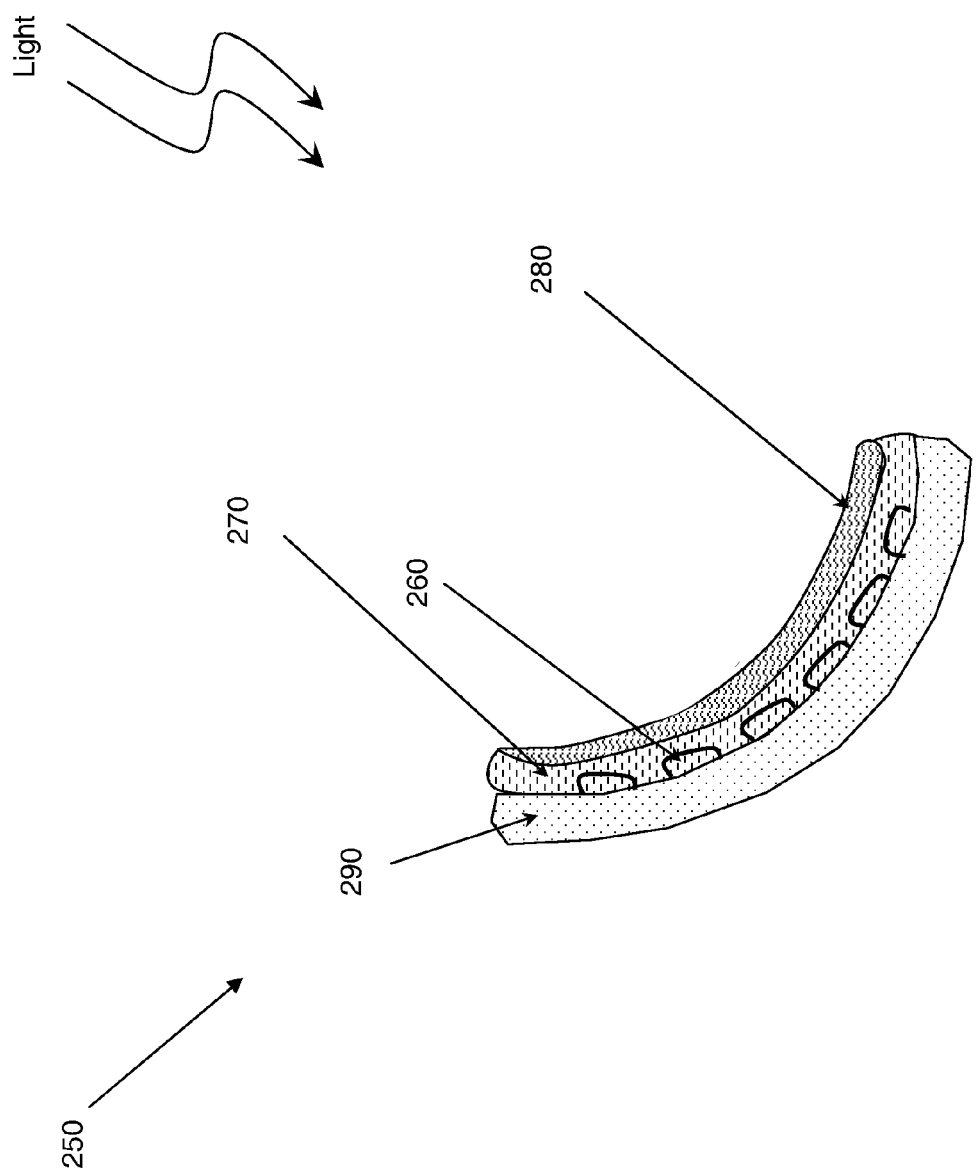

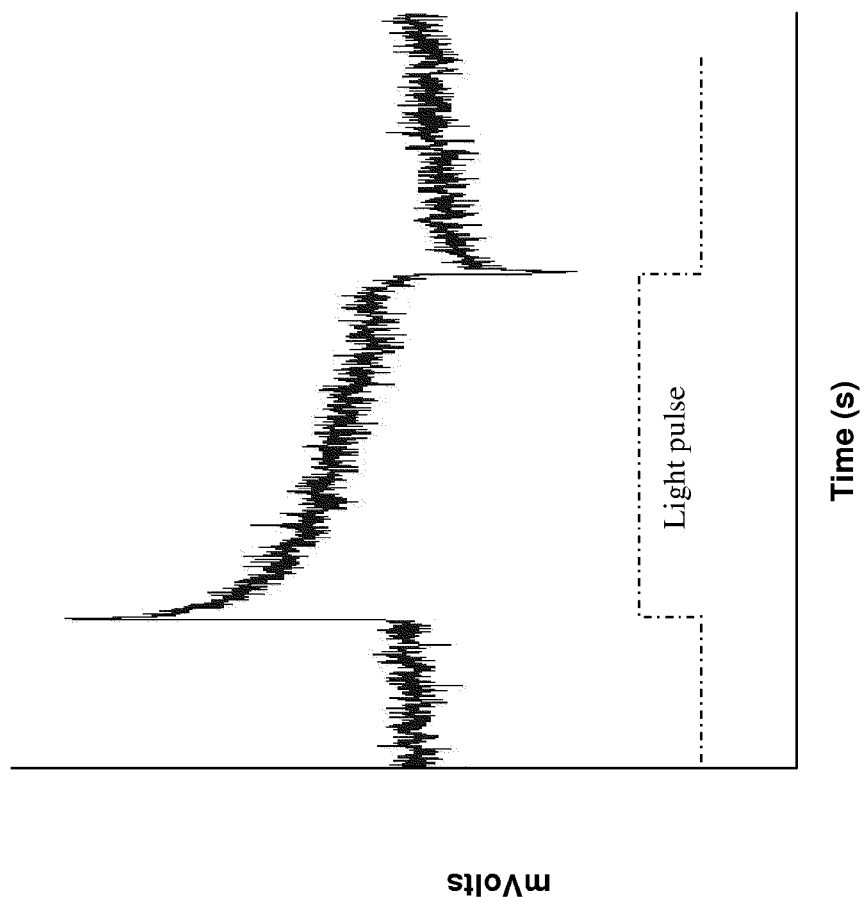

ARTIFICIAL RETINA DEVICE

CROSS-REFERENCE TO RELATED APPLICATIONS

The present application is a U.S. national stage application under 35 U.S.C §371 claiming the benefit of International Application No. PCT/IB2010/002170, filed on Sep. 2, 2010, which claims the benefit of Indian Application No. 1822/CHE/2010, filed on Jun. 28, 2010, the entire contents of which are incorporated herein by reference in their entireties.

BACKGROUND

The following description is provided to assist the understanding of the reader. None of the information provided or references cited is admitted to be prior art.

When light is received by a retina, complex signal processing takes place within the layers of the retina. Visual signals encode the information in the form of electrical "spikes." These electrical "spikes" are actually electro-chemical signals sent from ganglion cells to the visual cortex in the brain via the optic nerve. In some vision related diseases, the outer layers of the retina including the photoreceptors lose their function. However, the inner layers of the retina remain anatomically and functionally intact.

Advances have been made in the use of microphotodiode arrays and patterned stimulation electrodes as artificial retina devices. Such artificial retina devices are designed to address various vision related diseases such as retinal pigmentosa or macular degeneration or to augment normal vision. However, known artificial retina devices involve conventional electronics that are based on inorganic materials such as silicon or platinum/iridium oxide coated substrates. Such devices are not biocompatible or bio-stable and thus involve serious drawbacks to implantation in a human eye.

The drawbacks associated with traditional artificial retina devices are numerous. Such devices are known to cause serious gliosis in in-vivo cases as well as additional complications due to the mechanical incompatibility of the device with human tissue at the implant/tissue interface. In addition, such devices require bio-compatible electrodes in order to interface with human tissue and a video chip to process signals. Such devices further require an external power supply which may be provided via radio frequency signals or pulsed energy systems. In addition, traditional artificial retina devices have low visual acuity despite numerous advances in many areas (e.g., material, fabrication, energy supply, packaging, etc.). For example, traditional devices have allowed for a maximum of only 20/100 vision.

SUMMARY

The present technology provides an illustrative artificial retina device that includes a substrate and an array of micro-electrodes formed on the substrate. The artificial retina device further includes a photoconducting polymer blend deposited on the array of micro-electrodes. The photoconducting polymer blend is configured to produce excited charge carriers in response to receiving light.

The illustrative artificial retina device may further include an interface between at least one electrode of the array of micro-electrodes and the photoconducting polymer blend, such that the interface is configured to accumulate the excited charge carriers and produce a voltage change with respect to a ground. In an embodiment, the ground is an electrolyte of an electrolyte layer. The electrolyte layer may be formed over the photoconducting polymer blend, wherein the ground comprises the electrolyte layer. The electrolyte layer may be one of a salt solution or a gel. In an alternative embodiment, the ground may be another electrode of the array of micro-electrodes.

The array of micro-electrodes of the illustrative artificial retina device may be positioned adjacent to neurons such that the array of micro-electrodes convey an electrical signal corresponding to the voltage change to the neurons. The electrodes of the array of micro-electrodes may includes an electrically conducting polymer such as poly(3,4-ethylenedioxythiophene):poly(4-styrene sulfonate) (PEDOT:PSS).

The substrate of the illustrative artificial retina device may be flexible and may comprise glass, plastic, or a biocompatible composite. The photoconducting polymer blend may include at least one of a polythiophene or polyparaphenylene vinylene derivative. In an embodiment, the photoconducting polymer blend may be P3HT(poly3hexylthiophene)-PCBM. The photoconducting polymer blend may be transparent or semi-transparent.

In an embodiment, the photoconducting polymer blend comprises one or more pixels that are sensitive to respective wavelengths of the light spectrum. The one or more pixels may have different compositions of a photoconducting polymer or may have different thicknesses of the photoconducting polymer blend. In an embodiment, the pixels are configured to detect one of two colors and convey a electrical signals comprising a positive and negative spikes in response to the detection of the respective colors.

The illustrative artificial retina device may have several geometries. For example, the array of micro-electrodes may deposited directly on the substrate and be substantially encompassed by the photoconducting polymer blend. In addition, an electrically conducting polymer may be positioned between the substrate and the photoconducting polymer blend. The illustrative artificial retina device may also include an electrolyte layer positioned between the substrate and the photoconducting polymer blend. In addition, the array of micro-electrodes and the photoconducting polymer blend may be positioned between the electrolyte and the substrate.

The present technology further provides an illustrative method of manufacturing an artificial retina device. The method includes forming an array of micro-electrodes on a substrate and applying a photoconducting polymer blend over the array of micro-electrodes. The photoconducting polymer blend is configured to produce excited charge carriers in response to receiving light.

In an embodiment, forming an array of micro-electrodes on a substrate comprises spin coating poly(3,4-ethylenedioxythiophene):poly(4-styrene sulfonate) (PEDOT:PSS) over a patterned electrode that includes indium tin oxide or platinum or silicon nitride-coated glass. The illustrative method may further include heating the array of micro-electrodes to improve the adhesion of the PEDOT:PSS to the patterned electrode.

In an embodiment, applying a photoconducting polymer may include forming an interface between at least one electrode of the array of micro-electrodes and the photoconducting polymer blend. The interface is configured to accumulate the excited charge carriers and produce a voltage change with respect to a ground. The method may further include forming an electrolyte layer on the substrate. In an embodiment, the ground is the electrolyte layer. In an alternative embodiment, the ground may be another electrode of the array of micro-electrodes.

The substrate may be a flexible substrate that comprises glass, plastic, or a biocompatible composite, and the photoconducting polymer blend may include a polythiophene or polyparaphenylene vinylene derivative.

In an embodiment, the applying a photoconducting polymer blend over the array of micro-electrodes includes forming one or more pixels of the photoconducting polymer blend that are sensitive to respective wavelengths of the light spectrum. The forming one or more pixels of the photoconducting polymer blend may include forming the one or more pixels with different compositions of a photoconducting polymer or forming the one or more pixels with different thicknesses of the photoconducting polymer blend.

In another embodiment, the applying a photoconducting polymer blend over the array of micro-electrodes includes substantially encompassing the array of micro-electrodes within the photoconducting polymer blend. The illustrative method may further include forming an electrolyte layer over the photoconductive polymer blend such that the array of micro-electrodes and the photoconducting polymer blend are positioned between the electrolyte and the substrate.

The present technology further provides an illustrative method of manufacturing an artificial retina device that includes forming a ground layer on a substrate and forming a photoconducting polymer blend on the ground layer. The method further includes depositing an array of micro-electrodes adjacent to the photoconducting polymer blend. The photoconducting polymer blend is configured to produce excited charge carriers in response to receiving light.

In an embodiment, the array of micro-electrodes is formed entirely from an electrically conducting polymer such as poly (3,4-ethylenedioxythiophene):poly(4-styrene sulfonate) (PEDOT:PSS).

In another embodiment, the depositing an array of micro-electrodes adjacent to the photoconducting polymer blend includes forming an interface between an electrode of the array of micro-electrodes and the photoconducting polymer blend. The interface is configured to accumulate the excited charge carriers and produce a voltage change with respect to a ground. The ground layer may comprise an electrically conducting polymer or an electrolyte.

In addition, the forming a photoconducting polymer blend may include forming one or more pixels of the photoconducting polymer blend that are sensitive to respective wavelengths of the light spectrum. The forming one or more pixels may include forming the one or more pixels with different compositions of a photoconducting polymer or forming the one or more pixels with different thicknesses of the photoconducting polymer blend.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIGS. 1a and 1c depict cross-sectional views of an organic material-based artificial retina device having first and second geometries in accordance with illustrative embodiments.

FIGS. 2a and 2b depict cross-sectional views of organic material-based artificial retina devices having third and fourth geometries in accordance with illustrative embodiments.

FIGS. 9a, 9b, and 9c depict outputs from an organic material-based artificial retina device of the present technology in accordance with an illustrative embodiment.

DETAILED DESCRIPTION

Figure 1B:
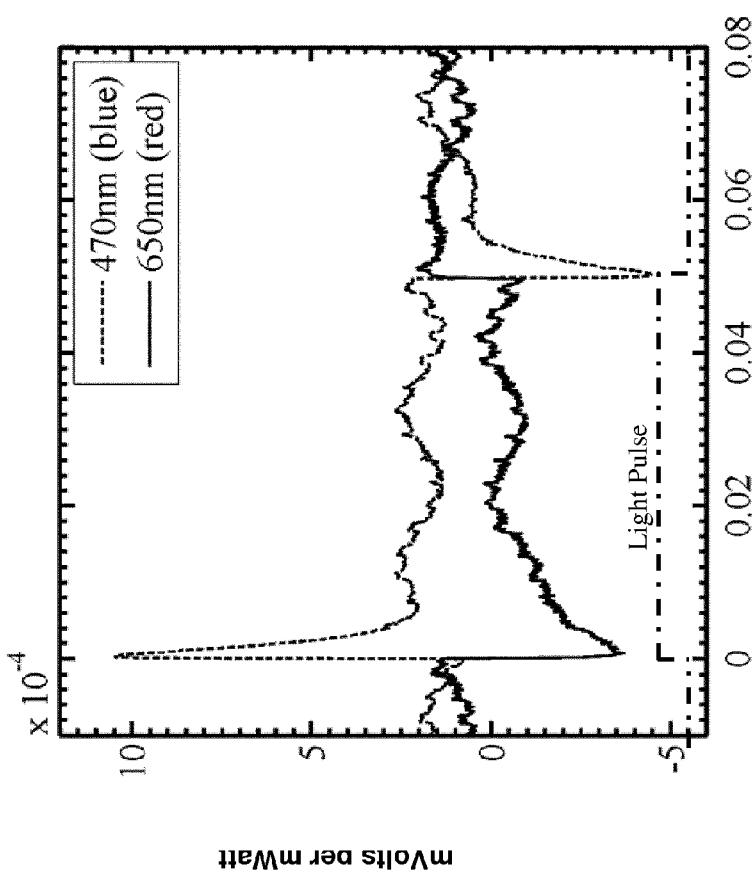
FIG. 1b depicts an output response from a photoconducting polymer blend of a device configured to two-color detection in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

There are a variety of issues associated with traditional artificial retina devices. These include, but are not limited to, the general incompatibility of such devices with biological tissue. Traditional artificial retina devices are made of inorganic materials that are incompatible with biological tissue, thus creating numerous complications that arise from the incompatibility of the device with tissue at the implant/tissue interface. Described herein are improved organic material-based artificial retina devices which include photoconducting semiconducting polymers as the active media. The polymeric nature of the active media allows for the utilization of the advantages of polymer mechanical attributes. Such devices are compatible and opto-electronically stable with most buffer solutions and biological tissue.

FIG. 1a depicts a cross-sectional view of an organic material-based artificial retina device 100 having a first geometry in accordance with an illustrative embodiment. Such a device may be configured for sub-retinal placement in an eye such that the electrode array is in electrical contact with associated cells, e.g., neurons such as photoreceptor cells. Artificial retina device 100 includes an array of micro-electrodes 110 formed on a photoconducting polymer blend 120. Micro-electrodes 110 may comprise any conducting material known to those of skill in the art. For example, micro-electrodes 110 may comprise platinum or a conductive, transparent material like indium tin oxide. In an alternative embodiment, micro-electrodes 110 may comprise a transparent or semi-transparent electrically conducting polymer such as poly(3,4-ethylenedioxythiophene):poly(4-styrene sulfonate) (PEDOT:PSS) which is formed on a substrate such as glass, plastic, biocompatible composite, or any other substrate material known to those of skill in the art. In an embodiment, each micro-electrode 110 is entirely made of an electrically conducting polymer such as PEDOT:PSS, thus allowing artificial retina device 100 to be formed without any metals or metal oxides.

Artificial retina device 100 further includes a photoconducting polymer blend 120 that is formed under the array of micro-electrodes 110. Photoconducting polymer blend 120 may comprise poly(3-hexylthiophene) P3HT, other polythiophene or polyparaphenylene vinylene derivatives as donor polymers, phenyl-C61-butyric acid methyl ester (PCBM), naphthalene or perylene diimide derivatives in molecular or polymer form as acceptors, or any other photoconducting polymer blend 120 known to those of skill in the art that is capable of sufficient photo-excitation of charge carriers. Example naphthalene or perylene diimide derivatives may include poly{[N,N"-bis(2-octyldodecyl)-naphthalene-1,4,5,8-bis(dicarboximide)-2,6-diyl]-alt-5,5"-(2,2"-bithiophene)} (P(NDI2OD-T2): Polyera Activink N2200), N,N'-dipyrimidinyl-3,4,9,10-perylene-tetracarboxylic diimide (DMP), or N-(1-nonyldecyl)perylene-3,4,9,10-tetracarboxyl-3,4-anhydride-9,10-imide). In an embodiment, photoconducting polymer blend 120 may be transparent or semi-transparent.

Photoconducting polymer blend 120 includes charge carriers that respond to light through photo-excitation. Upon receiving light at photoconducting polymer blend 120, charge carriers such as electrons within photoconducting polymer blend 120 become excited due to the absorption of photons, as further described below. The movement of the excited charge carriers causes an accumulation of the charge carriers at the interface between micro-electrodes 110 and photoconducting polymer blend 120. The accumulation of the charge carriers at the interface between micro-electrodes 110 and photoconducting polymer blend 120 will in turn cause a voltage change between micro-electrodes 110 and a ground which is sensed by cells, for example, neurons such as photoreceptor cells, associated with an eye.

Artificial retina device 100 further includes an electrolyte 130. Electrolyte 130 functions as a counter ground electrode and as a recipient of charges from the photoconducting polymer blend 120. As such, a potential may be established between electrolyte 130 and micro-electrodes 110. Electrolyte 130 may comprise a salt solution, a gel, or any other electrolyte known to those of skill in the art.

Artificial retina device 100 also includes a substrate 140 upon which the array of micro-electrodes 110, photoconducting polymer blend 120, and/or electrolyte 130 are formed. In FIG. 1a, electrolyte 130 is formed directly on substrate 140, photoconducting polymer blend 120 is formed on electrolyte 130, and the array of micro-electrodes 110 is formed directly on photoconducting polymer blend 120. The substrate 140 may comprise glass, plastic, biocompatible composites, or any other substrate known to those of skill in the art capable of use in artificial retina device 100. In an embodiment, substrate 140 is flexible, thus allowing for artificial retina device 100 to be securely and comfortably placed within the eye of a patient. In an alternative embodiment, the array of micro-electrodes may be formed directly on a substrate as described below with respect to FIGS. 2a and 2b, and a photoconducting polymer blend may then be formed over and around the array of micro-electrodes, and an electrolyte may be formed on the photoconducting polymer blend.

As discussed above, upon receiving light, charge carriers within photoconducting polymer blend 120 become excited due to the absorption of photons. The combination of polymers within the photoconducting polymer blend mimics retinal (retinaldehyde, vitamin A aldehyde). Photoconducting polymer blend 120 of artificial retina device 100 exhibits light-induced generation and movement of the charge carriers. Photoconducting polymer blend 120 is stimulated regionally by the absorption of photons, i.e., excited charge carriers are formed in the areas of photoconducting polymer blend 120 which receive light. The movement of the excited charge carriers results in an accumulation of the excited charge carriers at an interface between the stimulated region of photoconducting polymer blend 120 and a respective micro-electrode 110 adjacent to the stimulated region of photoconducting polymer blend 120. This, in turn, causes the formation of a potential between the respective micro-electrode 110 and the ground. In an embodiment, the ground may be another micro-electrode of the array of micro-electrodes 110. In an alternative embodiment, the ground is a buffer solution such as electrolyte 130 which is adjacent to photoconducting polymer blend 120.

The change in potential/voltage between micro-electrodes 110 and the ground is "sensed" by cells, for example neurons such as photoreceptor cells (e.g., rods, cones, etc.) associated with the eye or in proximity to artificial retina device 100. In alternative embodiments, the neurons are ganglion cells. Accordingly, micro-electrodes 110 stimulate the photoreceptor cells associated with the eye or in proximity to artificial retina device 100, thus providing an appropriate electrical signal to the photoreceptor cells based ultimately on the light received within various regions of photoconducting polymer blend 120. As a result of the changes in potential at micro-electrodes 110 in response to received light, the photoreceptor cells receive signals that mimic signal spikes which would be received in a normal visual photoreceptor layer of the eye.

Artificial retina device 100 is configured to detect light in the visible spectrum. In alternative embodiments, artificial retina device 100 may also be configured to detect light in the infrared region of the electromagnetic spectrum. In accordance with an illustrative embodiment, photoconducting polymer blend 120 includes different compositions which are sensitive to different wavelengths of the light spectrum. Photoconducting polymer blend 120 can be selectively pixellated so that each pixel is sensitive to a different wavelength of the light spectrum, rather than having a single continuous composition across the device. For example, poly(para-phenylene) may be used to detect yellow colors, polyfluorines may be used to detect blue colors, and poly(3-hexylthiophene) derivatives may be used to detect green and red colors. In an alternative embodiment, different thicknesses of photoconducting polymer blend 120 may sensitive to different wavelengths of the light spectrum. The thickness of photoconducting polymer blend 120 may range from 0.1 microns to 50 microns. In an embodiment, a photoconducting polymer blend having a thickness of greater than 1 micron are used to detect red light while a photoconducting polymer blend having a thickness of less than 200 nm is used to detect blue or green light. Accordingly, photoconducting polymer blend 120 can be pixellated such that different pixels have different thicknesses of the photoconducting polymer blend. As such, the different pixels will be sensitive to different wavelengths of light. The pixels are, in turn, associated with one or more electrodes of micro-electrode array 110.

In an embodiment, artificial retina device 100 may also be configured for color contrast according to a two-color detection scheme using a photoconducting polymer blend having a uniform composition and thickness. According to such an embodiment, the uniform composition of photoconducting polymer blend has a given thickness that will produce electrical signals in the form of a positive or a negative spike in response to receiving light of a first color or a second color, respectively. For example, upon receiving a red light at the photoconducting polymer blend having a characteristic thickness, an electrical signal having a negative spike will be generated. In contrast, upon receiving a blue light at the same photoconducting polymer blend having the same characteristic thickness, an electrical signal having a positive spike will be generated. Accordingly, the red and blue colors can be differentiated based on the polarity of the generated electrical spike.

FIG. 1b depicts an output response generated by a photoconducting polymer blend of a device configured for two-color detection in accordance with an illustrative embodiment. The device associated with FIG. 1b is configured to detect one of two colors. The two colors red (e.g., light having a wavelength of around 650 nm) and blue (e.g., light having a wavelength of around 470 nm), although any two colors may be used depending on the selected thickness of the pixels of photoconducting polymer blend 120 as discussed in the preceding paragraph. The device includes a photoconducting polymer blend layer having a thickness of between 250 and 300 nm and that comprises a blend of poly(3-hexylthiophene) and an acceptor polymer having a 1:1 ratio. The photoconducting polymer blend was dissolved in chlorobenzene and cast on indium-tin-oxide, where it was cured at 80° C. A potassium chloride solution was used as the electrolyte, and a platinum coated glass was used as the counter electrode. The device comprises an active surface area of about 12 mm$^2$. A light-emitting diode was used as the light source and was driven by a function generator.

As illustrated in FIG. 1b, in response to the device receiving a blue light (i.e., a light having a wavelength of around 470 nm), an electrical spike having a positive polarity is initially generated. In contrast, a red light (i.e., a light having a wavelength of around 650 nm) causes the generation of electrical spikes having opposite polarities to that of the electrical spikes generated in response to the reception of blue light. For example, in response to the device receiving the red light pulse having a 0.05 second duration, an electrical spike having a negative polarity is initially generated. Accordingly, such a device provides for the generation of opposite polarity electrical spikes that allow for the differentiation of red and blue wavelength light. It should be noted that the device as described above, when modified to have a much smaller or greater thickness of the photoconducting polymer blend layer, e.g., a thickness smaller than 200 nm or greater than 500 nm, does not exhibit opposite polarities in response to the reception of red and blue light, respectively. A second spike for each color appears when the 0.05 second long light pulse is turned off. As illustrated in FIG. 1b, the second spikes associated with the turning off of the red and blue light pulses have opposite polarities.

In alternative embodiments, a two-color detection scheme as described above may be utilized with devices other than that of artificial retina device 100 in order to discriminate between two colors and to generate an image. For example, a camera or other imaging device known to those of skill in the art may utilize the two-color detection scheme. Such a device may include one or more electrodes configured to detect and distinguish the polarity of the electrical signals produced by the photoconducting polymer blend in response to the reception of light. Such a device may further include a processor configured to receive and interpret the positive and negative spikes in order to differentiate between the two colors. The processor may be further configured to generate an image having color contrast based on the polarity of the spikes of the electrical signals. In an embodiment, the device may further comprise a display configured to display the generated image.

Artificial retina device 100 can have many alternative configurations/geometries according to various embodiments as described below with respect to FIGS. 1c, 2a, 2b, and 3. For example, the potential can be created laterally using one electrode of the array of micro-electrodes 110 as the ground. Alternatively, in a transverse geometry, photoconducting polymer blend 120 can be coated with a buffer solution such as electrolyte 130, which may act as the ground. While the potential from the device associated with the device that utilizes the electrode as a ground originates from transport of charge carriers across the polymer networks of photoconducting polymer blend 120, the device that utilizes the transverse geometry generates signals due to the charge transfer from photoconducting polymer blend 120 to electrolyte 130 or vice versa.

Figure 1C:
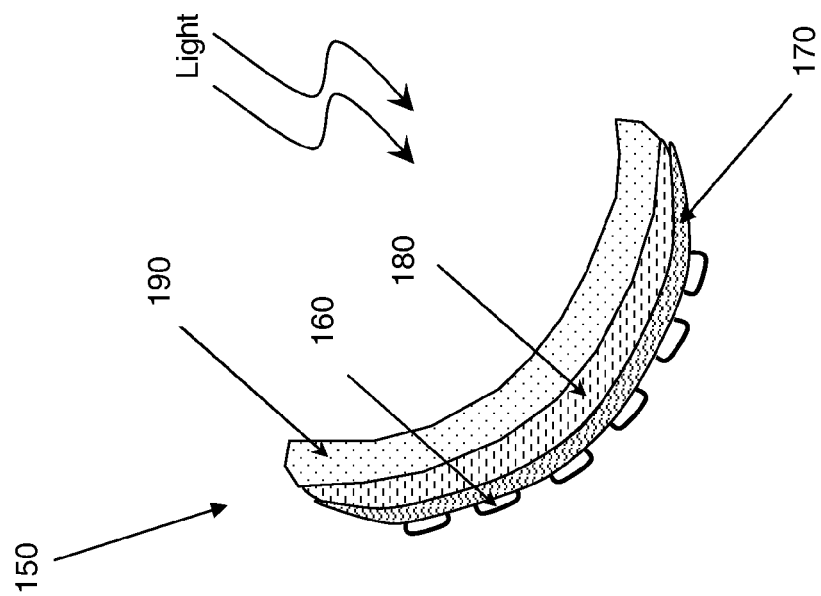

FIG. 1c depicts a cross-sectional view of another organic material-based artificial retina device 150 of the present technology having a second geometry in accordance with an illustrative embodiment. The device of FIG. 1c is configured for epi-retinal placement within an eye. Artificial retina device 150 of FIG. 1c includes a substrate 190 on which is formed an electrolyte 180. Photoconducting polymer blend 170 is formed on electrolyte 180. An array of micro-electrodes 160 is formed on photoconducting polymer blend 170. According to such a configuration, electrolyte 180 is once again configured as the ground.

As discussed above, upon receiving light, charge carriers within photoconducting polymer blend 170 become excited due to the absorption of photons. Photoconducting polymer blend 170 is stimulated regionally by the absorption of photons, i.e., excited charge carriers are formed in the areas of photoconducting polymer blend 170 which receive light. The movement of the excited charge carriers results in an accumulation of the excited charge carriers at an interface between the stimulated region of photoconducting polymer blend 170 and a respective micro-electrode 160 adjacent to the stimulated region of photoconducting polymer blend 170. This, in turn, causes the formation of a potential between the respective micro-electrode 160 and electrolyte 180 which acts as a ground.

The change in potential/voltage between micro-electrodes 160 and electrolyte 180 is "sensed" by ganglion cells. Accordingly, micro-electrodes 160 stimulate the ganglion cells associated with the eye or in proximity to artificial retina device 150, thus providing an appropriate electrical signal to the ganglion cells based ultimately on the light received within various regions of photoconducting polymer blend 170. As a result of the changes in potential at micro-electrodes 160 in response to received light, the ganglion cells receive signals that mimic signal spikes which would be received from a normal visual photoreceptor layer of the eye.

Figure 2A:
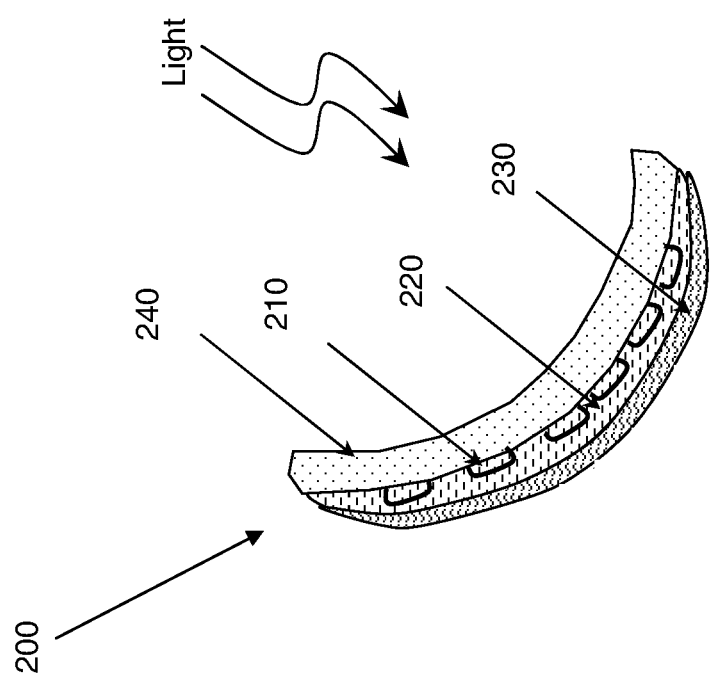

FIG. 2a depicts a cross-sectional view of an organic material-based artificial retina device 200 of the present technology having a third geometry in accordance with an illustrative embodiment. The device of FIG. 2a is configured for sub-retinal placement within an eye. Artificial retina device 200 of FIG. 2a includes an array of micro-electrodes 210 formed on a substrate 240. Photoconducting polymer blend 220 substantially encompasses the array of micro-electrodes 210 such that micro-electrodes 310 are surround by photoconducting polymer blend 220 except for a portion of micro-electrodes 210 that is adjacent to substrate 240. Electrolyte 230 is formed on photoconducting polymer blend 220. Accordingly, electrolyte 230 is configured as the ground. Artificial retina device 200 is thus configured to create a potential/voltage difference between micro-electrodes 210 and electrolyte 230 (which acts as the ground) that is received by photoreceptor cells associated with the eye or in proximity to artificial retina device 200. Accordingly, micro-electrodes 210 stimulate the photoreceptor cells associated with the eye or in proximity to artificial retina device 200, thus providing an appropriate electrical signal to the photoreceptor cells based ultimately on the light received within various regions of photoconducting polymer blend 220.

FIG. 2b depicts a cross-sectional view of another organic material-based artificial retina device 250 of the present technology having a fourth geometry in accordance with an illustrative embodiment. Artificial retina device 250 includes an array of micro-electrodes 260 formed on a substrate 290. Photoconducting polymer blend 270 substantially encompasses the array of micro-electrodes 260 such that micro-electrodes 260 are surround by photoconducting polymer blend 270 except for a portion of micro-electrodes 260 that is adjacent to substrate 290. Electrolyte 280 is formed on photoconducting polymer blend 270. Accordingly, electrolyte 280 is configured as the ground. Such a device is configured for epi-retinal placement in an eye. Artificial retina device 250 is thus configured to create a potential/voltage difference between micro-electrodes 260 and electrolyte 280 which is received by ganglion cells in a similar manner as described above with respect to FIG. 1c. Accordingly, micro-electrodes 260 stimulate the ganglion cells associated with the eye or in proximity to artificial retina device 250, thus providing an appropriate electrical signal to the ganglion cells based ultimately on the light received within various regions of photoconducting polymer blend 270.

Figure 3:
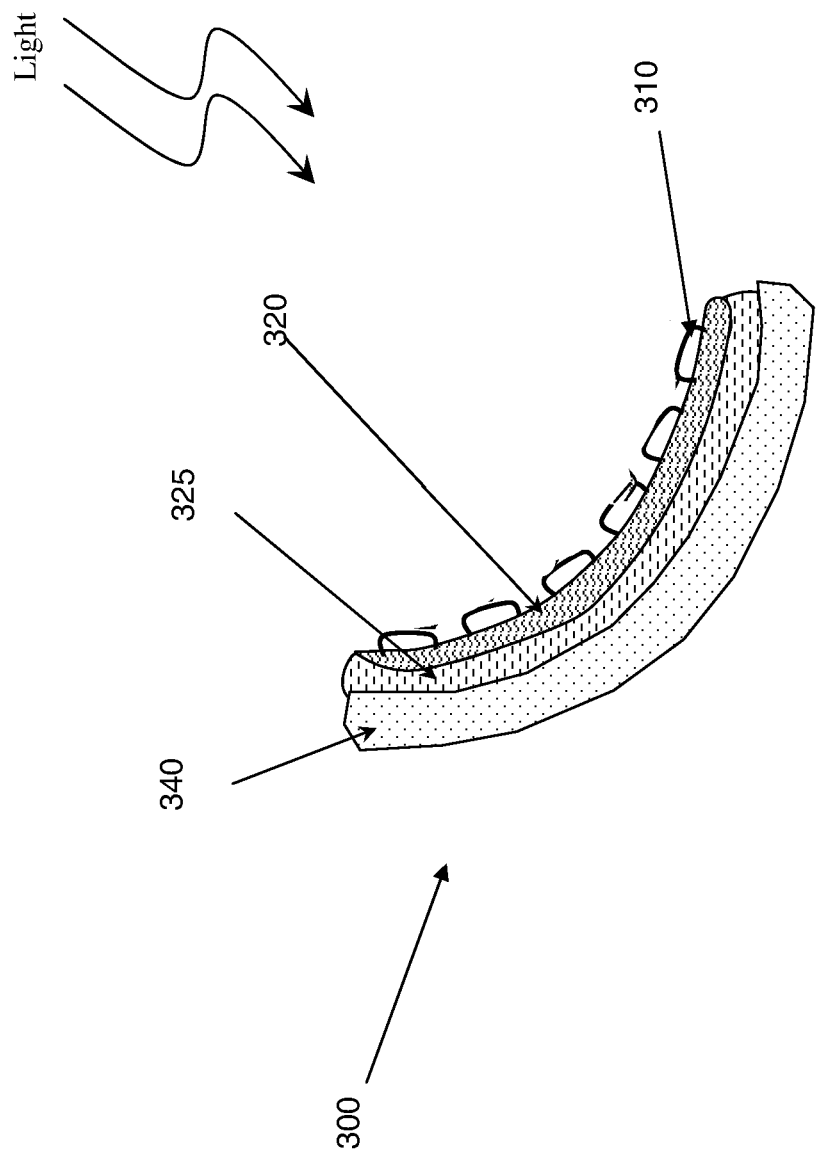
FIG. 3 depicts a cross-sectional view of an organic material-based artificial retina device having a fifth geometry in accordance with an illustrative embodiment.

FIG. 3 depicts a cross-sectional view of another organic material-based artificial retina device 300 of the present technology having a fifth geometry in accordance with an illustrative embodiment. Artificial retina device 300 includes a substrate 340 on which is formed an electrically conducting polymer 325. Electrically conducting polymer 325 is an organic polymer that conducts electricity. Photoconducting polymer blend 320 is formed on electrically conducting polymer 325. An array of patterned electrolyte 310 is patterned on photoconducting polymer blend 320. According to such an embodiment, electrically conducting polymer 325 acts as a ground electrode with which a potential is formed between the array of patterned electrolyte 310. In an embodiment, artificial retina device 300 comprises no metal micro-electrodes thus maximizing the compatibility of the device with human tissue. Such a device is configured for sub-retinal placement in an eye. Artificial retina device 300 is thus configured to create a potential/voltage difference between electrically conducting polymer 325 and the array of patterned electrolyte 310 that is received by photoreceptor cells that are associated with the eye or that are in proximity to artificial retina device 300. Accordingly, the array of patterned electrolyte 310 stimulates the photoreceptor cells, thus providing an appropriate electrical signal to the photoreceptor cells based ultimately on the light received within various regions of photoconducting polymer blend 320.

Figure 4:
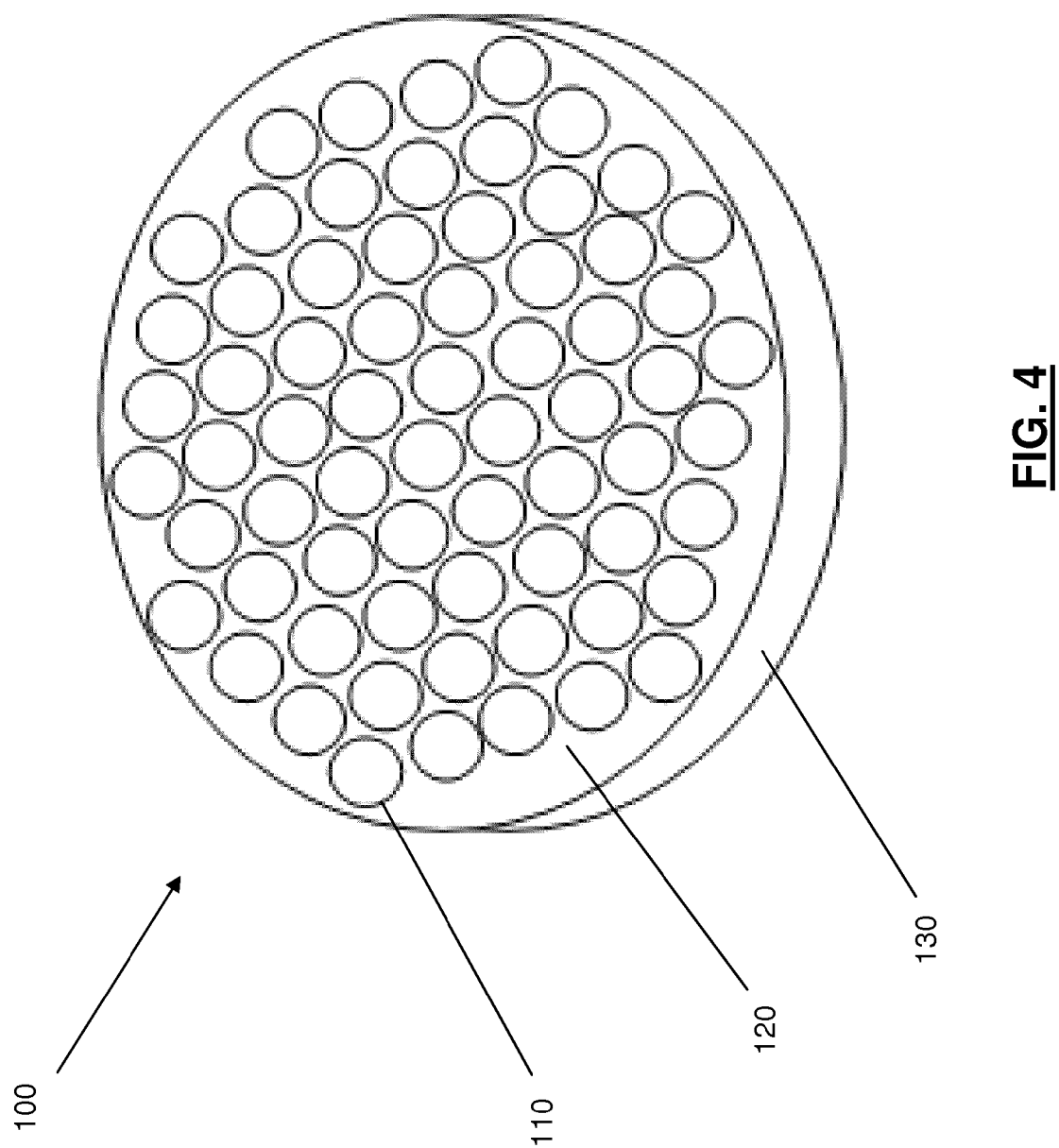
FIG. 4 depicts a top view of an organic material-based artificial retina device in accordance with an illustrative embodiment.

FIG. 4 depicts a top view of organic material based artificial retina device 100 in accordance with an illustrative embodiment. Note that FIG. 4 applies equally to artificial retina device 150 of FIG. 1c. Artificial retina device 100 of FIG. 4 includes the array of micro-electrodes 110, photoconducting polymer blend 120, and electrolyte 130. Micro-electrodes 110 of FIG. 4 comprise a circular cross-section from a top view. According to alternative embodiments, micro-electrodes 110 may have any shape known to those of skill in the art.

In an illustrative embodiment, micro-electrodes 110, 210, 260, and 310 have a diameter ranging from 10 microns to 100 microns and are spaced apart by a distance ranging from 30 microns to 400 microns. Accordingly, a 256 pixel by 256 pixel device may be formed in an area of 5 millimeters (mm) by 5 mm by spacing the individual micro-electrodes by about 10 microns. Density of the pixels may be in the range of 1000-2000 pixels per $mm^2$. Alternative diameters, distances, and densities are possible in alternative embodiments.

In an illustrative embodiment, the thickness of photoconducting polymer blends 120, 220, 270, and 320 may be varied from 50 nanometers (nm) to 200 nm and the thickness of the electrolyte layer may be around 10 microns thick. Alternative thicknesses are possible in alternative embodiments.

Figure 5:
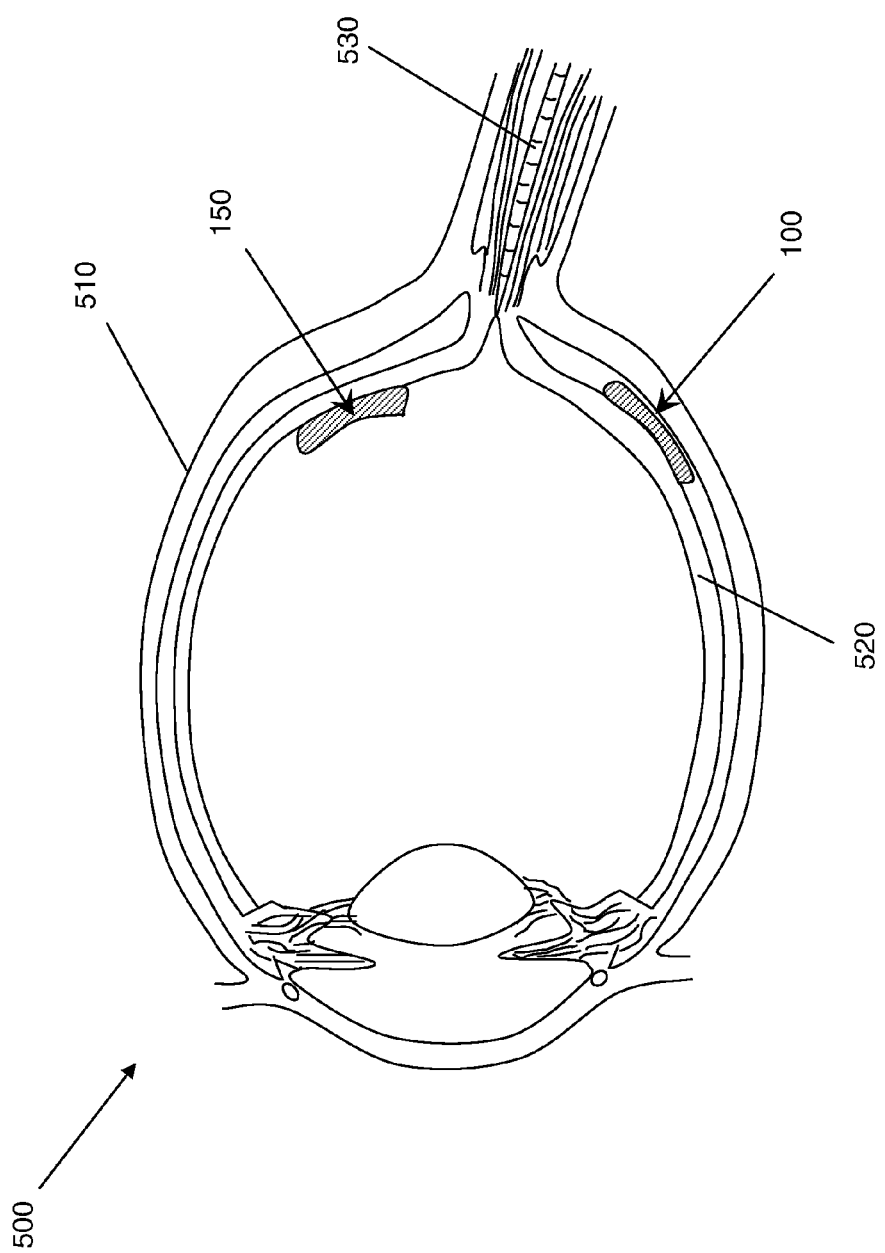
FIG. 5 is an illustration of sub-retinal and epi-retinal placements of organic material-based artificial retina devices within an eye of a patient in accordance with an illustrative embodiment.

FIG. 5 is an illustration of representative sub-retinal and epi-retinal placements of organic material-based artificial retina devices 100 and 150 within an eye 510 of a patient in accordance with an illustrative embodiment. An illustrative sub-retinal placement of a device within an eye is illustrated by artificial retina device 100 which is placed toward the back of eye 510 behind retina 520. An illustrative epi-retinal placement of a device within an eye is illustrated by artificial retina device 150 which is placed toward the back of eye 510 but in front of retina 520. As such, micro-electrodes of artificial retina devices 100 and 150 are in electrical contact with neurons such as photoreceptor cells or ganglion cells that communicate signals received from the micro-electrodes to optical nerve 530. In another embodiment, the micro-electrodes of artificial retina devices 100 and 150 are placed in contact with bipolar cells of the eye. In an embodiment, artificial retina devices such as those described with respect to FIGS. 2a and 2b are placed within the eye such that the substrates of the devices are in physical contact with the neurons, i.e., the ganglion cells or photoreceptor cells.

Figure 6:
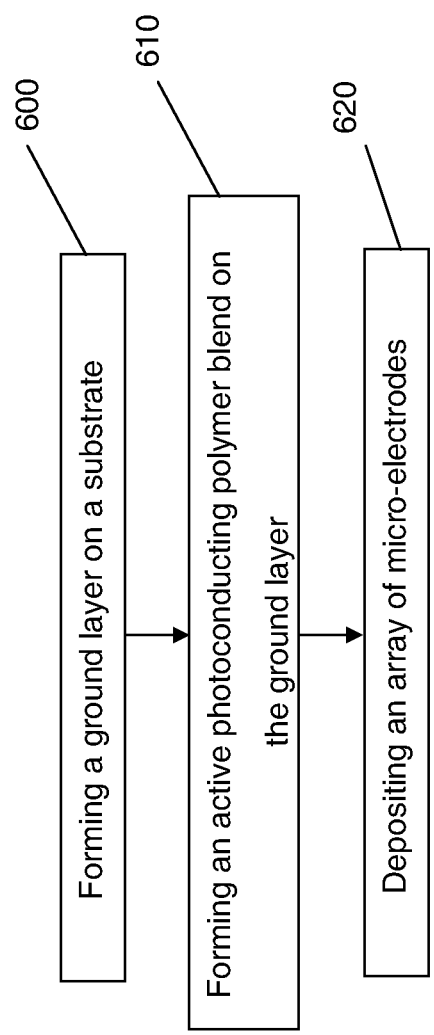
FIG. 6 depicts a method for producing an organic material-based artificial retina device of FIGS. 1a, 1c, and 3 in accordance with an illustrative embodiment.

FIG. 6 depicts a method for producing organic material-based artificial retina devices 100, 150, and 300 in accordance with an illustrative embodiment. In an operation 600, a ground layer is formed on a substrate. In an embodiment, the ground layer is an electrolyte. The electrolyte may comprise a salt solution, a gel, or any other electrolyte known to those of skill in the art. In an alternative embodiment, a micro-electrode layer is formed on the substrate and can be composed of electrically conducting polymer such as PEDOT: PSS which acts as a ground electrode. Accordingly, the ground layer comprises the ground point against which the potential at the subsequently deposited micro-electrode/photoconducting polymer blend interface is measured.

In an operation 610, a photoconducting polymer blend layer is formed on the ground layer. The photoconducting polymer blend may comprise poly(3-hexylthiophene)-phenyl-C61-butyric acid methyl ester (P3HT-PCBM), other polythiophene or polyparaphenylene vinylene derivatives, or any other photoconducting polymer blend known to those of skill in the art that is capable of sufficient photo-excitation of charge carriers. The photoconducting polymer blend includes charge carriers that respond to light through photo-excitation and that accumulate at the interface between the subsequently formed micro-electrodes and the photoconducting polymer blend layer causing a change in potential/voltage between the micro-electrodes and the ground layer. Other possible compounds which may serve as the photoconducting polymer blend include, but are not limited to, poly[N-9'-heptadecanyl-2,7-carbazole-alt-5,5-(4',7'-di-2-thienyl-2',1',3'-benzothiadiazole)] (PCDTBT), poly[2,6-(4,4-bis-(2-ethylhexyl)-4H-cyclopenta[2,1-b; 3,4-b_]-dithiophene)-alt-4,7-(2,1,3-benzothiadiazole)] (PCPDTBT) as donor polymers, and phenyl-C70-butyric acid methyl ester (PCBM-C70), poly[N,N'-bis(2-octyldodecyl)-naphthalene-1,4,5,8-bis(dicarboximide)-2,6-diyl]-alt-5,5'-(2,2'-bithiophene), (P(NDI2O-T2)), or perylene diimide and its derivatives as acceptor polymers.

In an operation 620, an array of micro-electrodes is formed on the photoconducting polymer blend layer. As discussed above, the micro-electrodes may comprise any conductive material known to those of skill in the art. For example, micro-electrodes may comprise platinum or a conductive, transparent material like indium tin oxide. In an illustrative embodiment, the micro-electrodes are printed on the photoconducting polymer blend layer to form patterns as desired for the particular application. In an alternative embodiment, the micro-electrodes may comprise only an electrically conducting polymer, for example PEDOT:PSS. Such a configuration allows artificial retina device 100 to be formed solely of organic materials, without the inclusion of any metals or metal oxides. The absence of metals and metal oxides in the device allows for better compatibility with the organic tissue in which the device is implanted. In an alternative embodiment, polypyrrole or any other electrically conducting, biocompatible polymer known to those of skill in the art may be utilized as the electrically conducting polymer.

Figure 7:
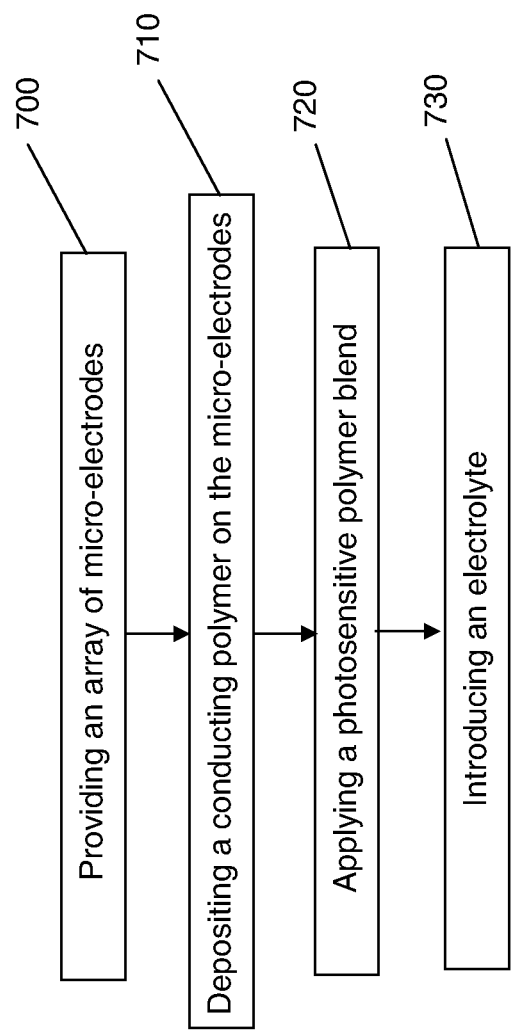
FIG. 7 depicts a method for producing an organic material-based artificial retina device of FIGS. 2a and 2b in accordance with an illustrative embodiment.

FIG. 7 depicts a method for producing organic material based artificial retina devices 200 and 250 in accordance with an illustrative embodiment. In an operation 700, an array of micro-electrodes is provided on a substrate according to any process known to those of skill in the art. In an illustrative embodiment, the micro-electrodes are printed on the substrate to form patterns as desired for the particular application. As discussed above, the micro-electrodes may comprise any conductive material known to those of skill in the art. For example, micro-electrodes may comprise platinum or a conductive, transparent material like indium tin oxide.

In an operation 710, an electrically conducting polymer is deposited on the array of micro-electrodes. According to an illustrative embodiment, the deposition of the electrically conducting polymer may be accomplished by spin coating PEDOT:PSS on the micro-electrodes.

In an alternative embodiment, the micro-electrodes provided in operation 700 may comprise only an electrically conducting polymer, for example PEDOT:PSS. According to such an embodiment, operation 710 is not performed because the electrodes already include an electrically conducting polymer. As such, each micro-electrode 110 is entirely made of an electrically conducting polymer such as PEDOT:PSS, thus allowing artificial retina device 100 to be formed solely of organic materials, without the inclusion of any metals or metal oxides. In an alternative embodiment, polypyrrole or any other electrically conducting, biocompatible polymer known to those of skill in the art may be utilized as the electrically conducting polymer.

In an operation 720, a photoconducting polymer blend is applied over or around the array of micro-electrodes. The photoconducting polymer blend may comprise poly(3-hexylthiophene)-phenyl-C61-butyric acid methyl ester (P3HT-PCBM), other polythiophene or polyparaphenylene vinylene derivatives, or any other photoconducting polymer blend known to those of skill in the art that is capable of sufficient photo-excitation of charge carriers. The photoconducting polymer blend includes charge carriers that respond to light through photo-excitation and that accumulate at the interface between the micro-electrodes and the photoconducting polymer blend causing a change in potential or voltage between the micro-electrodes and a ground. Other possible compounds which may serve as the photoconducting polymer blend include, but are not limited to, poly[N-9'-heptadecanyl-2,7-carbazole-alt-5,5-(4',7'-di-2-thienyl-2',1',3'-benzothiadiazole)] (PCDTBT), poly[2,6-(4,4-bis-(2-ethylhexyl)-4H-cyclopenta[2,1-b; 3,4-b_]-dithiophene)-alt-4,7-(2,1,3-benzothiadiazole)] (PCPDTBT) as donor polymers, and phenyl-C70-butyric acid methyl ester (PCBM-C70), poly[N,N'-bis(2-octyldodecyl)-naphthalene-1,4,5,8-bis(dicarboximide)-2,6-diyl]-alt-5,5'-(2,2'-bithiophene), (P(NDI2OD-T2)), or perylene diimide and its derivatives as acceptor polymers.

In an operation 730, an electrolyte is formed adjacent to the photoconducting polymer blend. The electrolyte may comprise a salt solution, a gel, or any other electrolyte known to those of skill in the art. In an embodiment, the electrolyte comprises a ground against which the potential at the micro-electrode/photoconducting polymer blend interface is measured.

Figure 8:
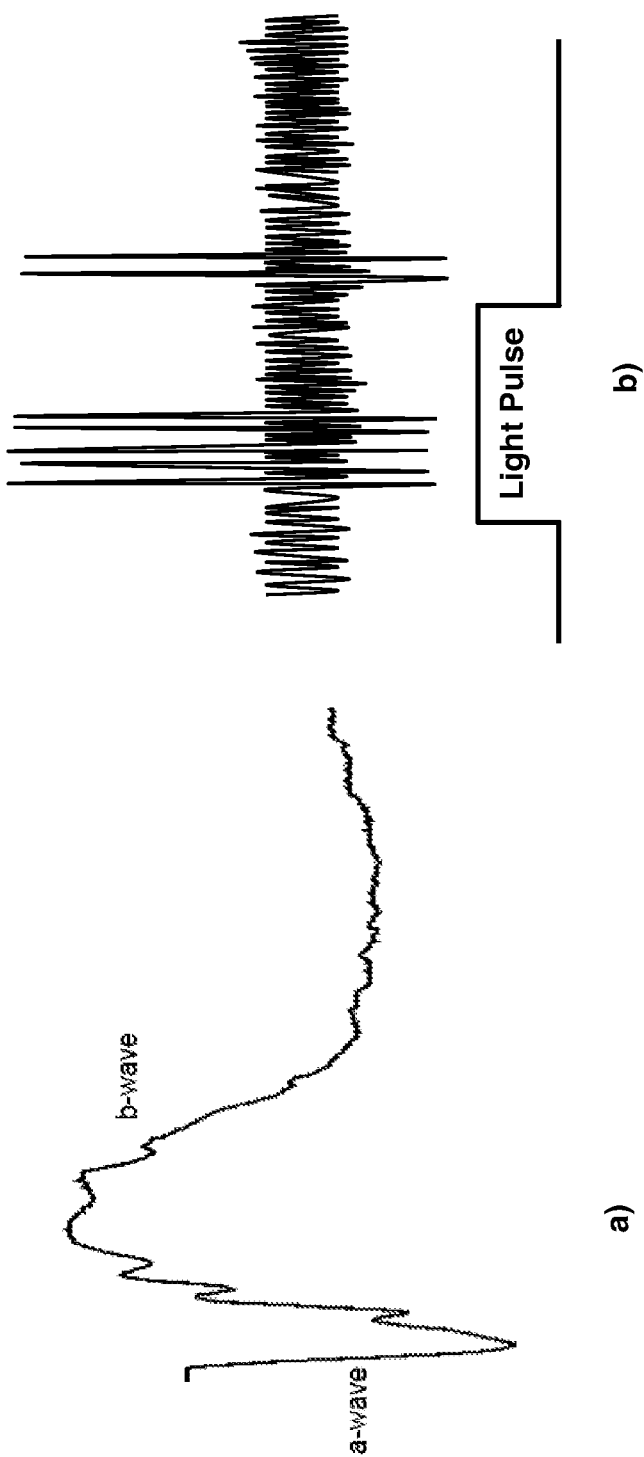
FIGS. 8a and 8b depict an output response of a normal mammalian retina in accordance with an illustrative embodiment.

FIGS. 8a and 8b depict an output response of a normal mammalian retina in accordance with an illustrative embodiment. FIG. 8b further illustrates an output response of the ganglion cells of the normal mammalian retina.

Figures 9A, 9B:
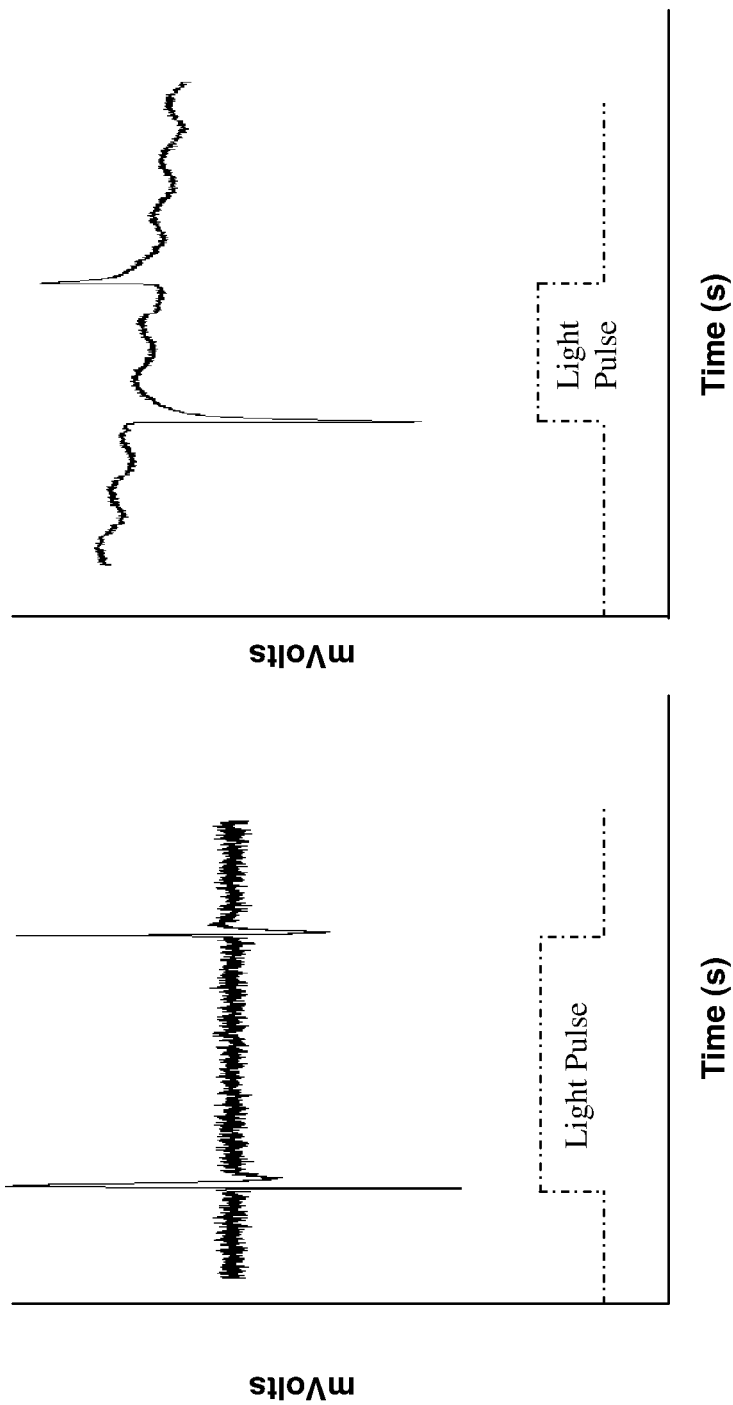

FIG. 9a depicts a filtered real time output from organic material-based artificial retina devices similar to artificial retina devices 100 and 150 in accordance with an illustrative embodiment. The device of the illustrative embodiment included a micro-electrode array of platinum electrodes having a diameter of 40 microns and inter-electrode spacing of 200 microns. A photoconducting polymer blend of donor-acceptor polymers was used. A potassium chloride solution having a concentration of 100 millimoles per liter was used as the electrolyte. The device included ground electrodes that were formed from silver/silver chloride. The data was measured across each electrode with respect to the ground and recorded using a data acquisition card at a sampling rate of 25 kHz. Light from a light emitting diode was pulsed using a function generator and was thereby used as a stimulus. A digital Butterworth filter was used to filter the signal. The filter was set from 200 Hz to 3 kHz.

FIG. 9b depicts an unfiltered real time output from the same organic material-based artificial retina device used for FIG. 9a. FIG. 9c depicts an output from the same organic material-based artificial retina device, except that the micro-electrode array of platinum electrodes of the device of FIGS. 9a and 9b was replaced with electrodes formed from electrically conducting polymer PEDOT:PSS. As demonstrated in the various figures, the field response from the devices in FIGS. 9a, 9b, and 9c is similar to the field response of the retina shown in FIGS. 8a and 8b, thus demonstrating the ability of the devices from FIGS. 9a, 9b, and 9c to stimulate the ganglion cells within the eye and ultimately the optic nerve cells. The greatest magnitude spikes have a value in the range of 15-20 millivolts (as demonstrated along the y-axis). The x-axis corresponds to time. The graphs of FIGS. 9a, 9b, and 9c illustrate readings taken over a duration of one second.

One or more flow diagrams may have been used herein. The use of flow diagrams is not meant to be limiting with respect to the order of operations performed. The herein described subject matter sometimes illustrates different components contained within, or connected with, different other components. It is to be understood that such depicted architectures are merely illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. An artificial retina device comprising:
   a substrate;
   an array of micro-electrodes formed over the substrate; and
   a photoconducting polymer blend positioned adjacent to the array of micro-electrodes to form an interface between at least one electrode of the array of micro-electrodes and the photoconducting polymer blend, wherein the photoconducting polymer blend is configured to produce excited charge carriers in response to receiving light, and wherein the interface is configured to accumulate the excited charge carriers and produce a voltage change with respect to a ground.

2. The apparatus of claim 1, further comprising an electrolyte layer formed adjacent to the photoconducting polymer blend, wherein the ground comprises the electrolyte layer.

3. The apparatus of claim 1, wherein the array of micro-electrodes is deposited directly on the substrate and is substantially encompassed by the photoconducting polymer blend.

4. The apparatus of claim 1, wherein the photoconducting polymer blend comprises at least one of a polythiophene or polyparaphenylene vinylene derivative.

5. The apparatus of claim 1, wherein the electrodes of the array of micro-electrodes comprise an electrically conducting polymer.

6. The apparatus of claim 5, wherein the electrically conducting polymer is poly(3,4-ethylenedioxythiophene):poly(4-styrene sulfonate) (PEDOT:PSS), and wherein the photoconducting polymer blend comprises P3HT (poly3hexylthiophene)-PCBM.

7. The apparatus of claim 1, wherein the photoconducting polymer blend comprises one or more pixels that are sensitive to respective wavelengths of the light spectrum, and wherein the one or more pixels comprise different compositions of a photoconducting polymer or different thicknesses of the photoconducting polymer blend.

8. The apparatus of claim 1, wherein at least a portion of the photoconducting polymer blend comprises a given thickness and is configured to detect a first color of two colors and convey a first electrical signal comprising a positive spike in response to the detection of the first color, and detect a second color of the two colors and convey a second electrical signal comprising a negative spike in response to the detection of the second color.

9. The apparatus of claim 1, further comprising an electrically conducting polymer positioned between the substrate and the photoconducting polymer blend, and wherein the micro-electrodes comprise an electrolyte.

10. The apparatus of claim 1, wherein the array of micro-electrodes is configured to be positioned adjacent to neurons to convey an electrical signal corresponding to the voltage change to the neurons.

11. The artificial retina device of claim 1, wherein the photoconducting polymer blend comprises a combination of photoconducting polymers that mimics retinal.

12. The artificial retina device of claim 1, wherein the photoconducting polymer blend comprises a combination of photoconducting polymers, and wherein the photoconducting polymers are each suitable for detection of different specific wavelengths of light.

13. A method of manufacturing an artificial retina device, the method comprising:
   forming an array of micro-electrodes over a substrate; and
   forming a photoconducting polymer blend over the substrate, wherein the photoconducting polymer blend is configured to produce excited charge carriers in response to receiving light, wherein the photoconducting polymer blend and the array of micro-electrodes form an interface between at least one electrode of the array of micro-electrodes and the photoconducting polymer blend, and wherein the interface is configured to accumulate the excited charge carriers and produce a voltage change with respect to a ground.

14. The method of claim 13, further comprising:
   forming a ground layer on the substrate, wherein the ground layer comprises the ground;
   forming the photoconducting polymer blend on the ground layer; and
   depositing the array of micro-electrodes adjacent to the photoconducting polymer blend.

15. The method of claim 14, wherein the ground layer comprises an electrolyte.

16. The method of claim 13, wherein the array of micro-electrodes is formed entirely from an electrically conducting polymer that comprises poly(3,4-ethylenedioxythiophene):poly(4-styrene sulfonate) (PEDOT:PSS).

17. The method of claim 13, wherein the forming a photoconducting polymer blend over the substrate comprises substantially encompassing the array of micro-electrodes within the photoconducting polymer blend, the method further comprising forming an electrolyte layer over the photoconductive polymer blend such that the array of micro-electrodes and the photoconducting polymer blend are positioned between the electrolyte and the substrate.

18. The method of claim 13, wherein the forming an array of micro-electrodes comprising forming an array of micro-electrodes on the substrate by spin coating poly(3,4-ethylenedioxythiophene):poly(4-styrene sulfonate) (PEDOT:PSS) over a patterned electrode.

19. The method of claim 13, wherein the forming a photoconducting polymer blend comprises forming one or more pixels of the photoconducting polymer blend, wherein the one or more pixels are sensitive to respective wavelengths of the light spectrum.

20. The method of claim 19, wherein the forming one or more pixels of the photoconducting polymer blend comprises one of forming the one or more pixels with different compositions of a photoconducting polymer or forming the one or more pixels with different thicknesses of the photoconducting polymer blend.

21. An apparatus comprising:
   an electrode; and
   a photoconducting polymer blend positioned adjacent to the electrode, wherein at least a portion of the photoconducting polymer blend is configured to:
      in response to receiving a light having a first color of two colors and without application of an external voltage to the electrode or photoconducting polymer blend, cause the formation of a first electrical signal at the electrode, wherein the first electrical signal has a first polarity; and
      in response to receiving a light having a second color of the two colors and without application of an external voltage to the electrode or photoconducting polymer blend, cause the formation of a second electrical signal at the electrode, wherein the second electrical signal has a second polarity that is opposite from the first polarity.

22. The apparatus of claim 21, wherein the at least a portion of the photoconducting polymer blend has a uniform thickness and composition, the apparatus further comprising a ground, wherein the first and second electrical signals comprise a voltage difference between the electrode and the ground.

* * * * *

UNITED STATES PATENT AND TRADEMARK OFFICE
CERTIFICATE OF CORRECTION

| | | |
|---|---|---|
| PATENT NO. | : 9,037,251 B2 | Page 1 of 1 |
| APPLICATION NO. | : 13/124357 | |
| DATED | : May 19, 2015 | |
| INVENTOR(S) | : Narayan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 601 days.

Item (56), under "OTHER PUBLICATIONS", in Column 1, Line 54, delete "intemet:" and insert -- internet: --, therefor.

Specification:

In Column 1, Line 7, delete "35 U.S.C §371" and insert -- 35 U.S.C § 371 --, therefor.

In Column 5, Lines 29-30, delete "poly{[N,N"-bis(2-octyldodecyl)-naphthalene-1,4,5,8-bis(dicarboxi- mide)-2,6-diyl]-alt-5,5"-(2,2"-bithiophene)} (P(NDI2OD-T2): Polyera Activink N2200)," and insert -- poly{[N,N'-bis(2-octyldodecyl)-naphthalene-1,4,5,8-bis(dicarboximide)-2,6-diyl]-alt-5,5'-(2,2'-bithiophene)} (P(NDI2OD-T2): Polyera ActivInk N2200)," --, therefor.

Signed and Sealed this
Seventeenth Day of November, 2015

Michelle K. Lee
*Director of the United States Patent and Trademark Office*